United States Patent
Pasricha et al.

[11] Patent Number: 5,776,160
[45] Date of Patent: *Jul. 7, 1998

[54] WINGED BILIARY STENT

[75] Inventors: Pankaj Jay Pasricha; Anthony N. Kalloo, both of Columbia, Md.

[73] Assignees: Pankaj Pasricha; Anthony Kalloo

[*] Notice: The term of this patent shall not extend beyond the expiration date of Pat. No. 5,486,191.

[21] Appl. No.: 443,755

[22] Filed: May 18, 1995

Related U.S. Application Data

[62] Division of Ser. No. 190,465, Feb. 2, 1994, Pat. No. 5,486,191.

[51] Int. Cl.$^6$ .................................................. A61M 29/00
[52] U.S. Cl. .................................. 606/191; 128/897
[58] Field of Search ........................... 606/1, 191, 198, 606/200; 604/8, 264; 128/897–899

[56] References Cited

U.S. PATENT DOCUMENTS

| | | |
|---|---|---|
| 3,821,956 | 7/1974 | Gordhammer . |
| 4,459,318 | 7/1984 | Hyans . |
| 4,521,210 | 6/1985 | Wong . |
| 4,677,143 | 6/1987 | Laurin . |
| 4,699,611 | 10/1987 | Bowden . |
| 4,795,439 | 1/1989 | Guest . |
| 4,813,925 | 3/1989 | Anderson . |
| 4,846,791 | 7/1989 | Hattler . |
| 4,973,301 | 11/1990 | Nissenkorn . |
| 5,167,614 | 12/1992 | Tessmann . |
| 5,176,626 | 1/1993 | Soehendra . |
| 5,246,445 | 9/1993 | Yachia . |

FOREIGN PATENT DOCUMENTS

| | | |
|---|---|---|
| 88138 | 8/1896 | Germany . |
| 1641356 | 4/1991 | U.S.S.R. . |
| 1715364 | 2/1992 | U.S.S.R. . |
| 1759431 | 9/1992 | U.S.S.R. . |
| 105038 | 3/1917 | United Kingdom . |
| 189127 | 5/1923 | United Kingdom . |

*Primary Examiner*—Michael Buiz
*Assistant Examiner*—Nancy Mulcare
*Attorney, Agent, or Firm*—Cushman Darby & Cushman Intellectual Property Group of Pillsbury Madison & Sutro, LLP

[57] ABSTRACT

A stent, for example for maintaining the patency of a duct such as a biliary duct, is provided that includes a plurality of radially extending wings. The wings project from a core which has a guide wire or wire stylet lumen. Each of the wings preferably includes a plurality of minute, longitudinally extending grooves for bile flow even in the event of tumor ingrowth. Advantageously the core itself is preformed into a helical configuration.

12 Claims, 1 Drawing Sheet

WINGED BILIARY STENT

This is a division of patent application Ser. No. 08/190,465, filed Feb. 2, 1994, now U.S. Pat. No. 5,486,191.

BACKGROUND OF THE INVENTION

1. Field of the Invention

The present invention relates to a stent that can be used to maintain flow in ducts in the body and, more particularly, to a stent for biliary drainage in patients whose biliary channels are obstructed for example due to cancer or benign disease.

2. Description of the Related Art

There are at least 4,000 new cases of biliary cancer, and more than 25,000 cases of pancreatic cancer every year, and the incidence appears to be rising. These cancer present with jaundice, due to obstruction of the bile duct. Unfortunately, by the time this stage is reached the tumor is usually at an advanced stage and unresurrectable. Management at this stage, therefore, usually consists of palliation only.

Although surgical bypass procedures are effective for palliative purposes, most patients with these cancers are either too sick to undergo major surgery or have too short a life-span to make the operation worthwhile. For this reason, palliation of jaundice in these biliary cancers is most often done by the endoscopic insertion of a biliary stent or endoprosthesis across the obstructed area. These are of two types: 1) plastic, and 2) expandable metal stents. Both types of conventional stents have problems associated with their use. Conventional plastic stents tend to clog with debris and biofilm relatively early. Metal stents overcome this problem by providing a greater initial lumen but also tend to clog, in their case with tumor ingrowth. Also, metal stents are extremely expensive, about 20 times more expensive than plastic stents. Even further, the metal stents are technically more difficult to insert and once in place, can not be removed.

SUMMARY OF THE INVENTION

The present inventors have overcome the foregoing problems and have invented a stent that uses flow along surfaces and not flow within a center lumen to maintain fluid flow in biliary ducts or any other duct in a body.

Thus, it is an object of the present invention to provide a stent which combines the many advantages of a plastic stent while avoiding the problems with biofilm build-up and stent obstruction. A stent according to the proposed invention does not require lumenal flow through an obstructed center lumen, as in prior art devices. Instead, the invention relies on flow along a plurality of surfaces.

The foregoing and other objects are realized in accordance with the present invention by providing a stent comprising an elongated main body or core member having a guide wire or wire stylet and a plurality of wing elements extending outwardly from the core member. The wing elements may be uniformly distributed about the circumference of the core member. Each wing has a length at least about as great as a length of the core member and a width that is preferably substantially greater than a cross-sectional dimension of the core member. If a guideline or wire stylet is used to place the stent, the core member may have a small lumen defined centrally for placement of the guideline.

In accordance with the presently preferred embodiment, there are a plurality of wing elements and each wing has a plurality of grooves defined on each surface thereof for laminar fluid flow therealong. Further, the core itself may be helically twisted.

Other objects, features, and characteristics of the present invention as well as the methods of operation and functions of the related elements of the structure, and the combination of parts and economies of manufacture, will become more apparent upon consideration of the following detailed description and the appended claims with reference to the accompanying drawings, all of which form a part of this specification, wherein like reference numerals designate corresponding parts in the various figures.

DETAILED DESCRIPTION OF THE PRESENTLY PREFERRED EXEMPLARY EMBODIMENTS

Figure 1:
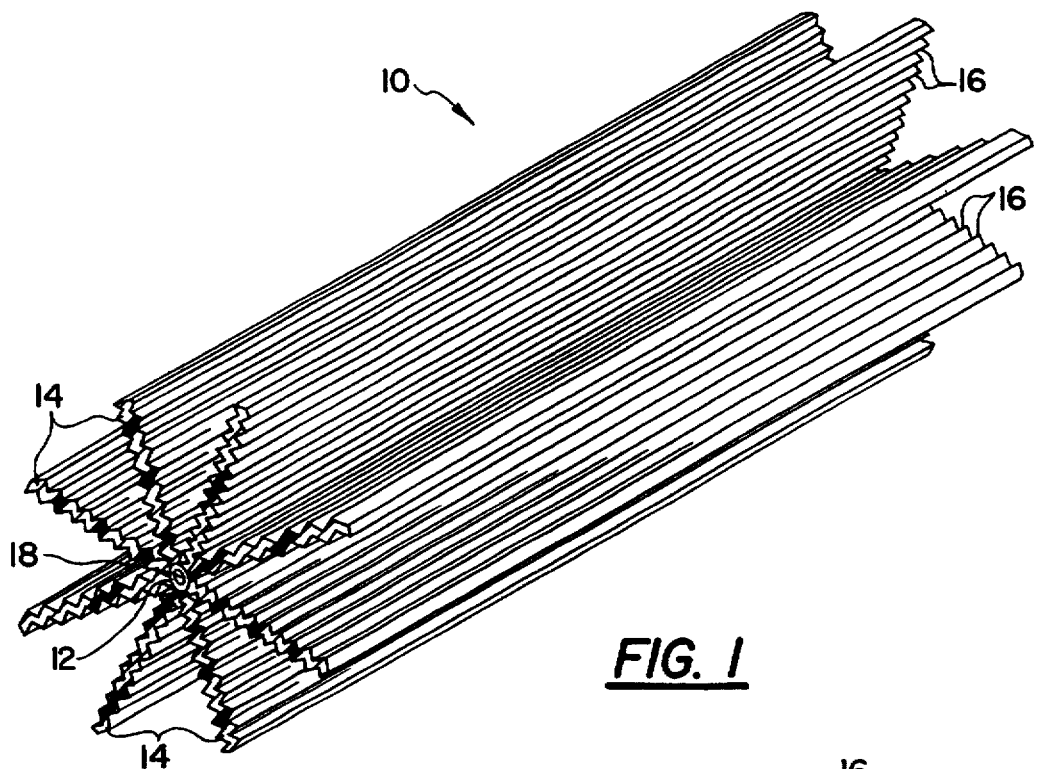
FIG. 1 is an enlarged schematic, partial perspective view of a stent provided in accordance with the invention.

In accordance with the present invention, a stent 10 is provided that includes an elongated core or main body 12 and a plurality of wings or fins 14 which extend generally radially from the core 12. In the illustrated embodiment, eight uniformly distributed fins 14 are provided. It is to be appreciated, however, that fewer or more fins may be found to be advantageous, depending upon the body passage or duct into which the stent 10 is adapted to be placed and the disposition of the fins 14 on the core 12.

In the illustrated embodiment, the wings or fins 14 each extend substantially continuously along the entire length of the core or main body 12. Furthermore, each fin or wing 14 is parallel to and extends longitudinally of the core 12. It is to be appreciated, however, that the invention is not necessarily limited to the illustrated configuration. The only requirement is that there are a plurality of surfaces that encourage flow along those surfaces.

Figure 2:
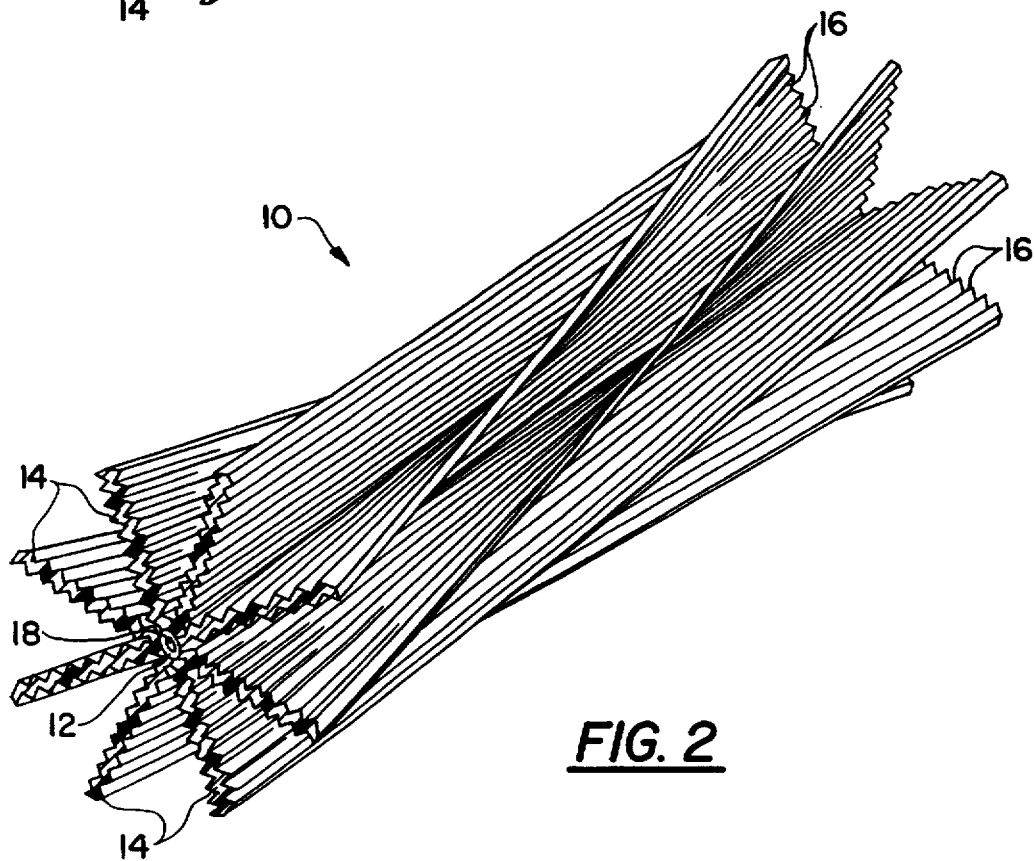
FIG. 2 is a view similar to FIG. 1, but of an alternative stent configuration in accordance with the invention.

In accordance with the most preferred embodiment, each of the wings 14 is grooved or corrugated on each side and/or the wings 14 are undulated, to define numerous small grooves 16 on each side for providing a capillary flow effect along the length thereof. The core 12' of the stent 10' may itself be twisted in a helical fashion or the wings 14' otherwise formed to describe a helix, as illustrated in FIG. 2.

There is no lumen as such through the core of the stent. Instead, a guide wire or wire stylet lumen 18 only is provided. Flow along the body passage in which the stent 10 is disposed, such as the bile duct, is therefore along the capillary like grooves 16 on the surfaces of the wings 14 and intermediate the wings 14. The grooves 16 provide more surface area, and, the greater the surface area the more fluid tension pulling fluid along. Thus, grooves 16 along the winged surface enhance flow by providing capillary like flow. Thus, by eliminating a large central lumen for flow, the turbulence in flow that inevitably results in biofilm formation has also been avoided. The foregoing was a major problem with conventional plastic stents.

The stent core 12 and wings 14 are preferably integrally formed from a plastic material such as polyethylene coated with a hydrophilic substance such as Hydromer so as to further reduce biofilm build-up. Tumor ingrowth is not expected to impair the function of the herein disclosed stent because the unique configuration of the stent will require that, to fully block flow, the tumor must physically grow into each of the channels 16, in each of the wings 14. Such ingrowth is extremely unlikely to occur during the expected lifetime of the patient. Other substances may also be incorporated into the surface coating the stent such as antibiotics (to inhibit bacterial growth), tumoricidal drugs or agents or other therapeutic substance.

The stent of the invention can be inserted endoscopically, percutaneously or surgically. Specifically, a guide wire (not shown) is first threaded through the obstructing lesion and beyond. Thereafter, the stent is threaded over the guide wire through stylet lumen 18. The stent is then pushed through the obstructing lesion with a pusher tube (not shown) which is placed in surrounding relation to the guide wire as well, in the usual fashion. The pusher tube and guide wire are then removed.

While the invention as been disclosed in particular with reference to bile duct obstruction, it is to be appreciated that the stent of the invention may useful in the event of pancreatic lesions or indeed a variety of ductal obstructions in other sites of the body such as in the urethra, fallopian tubes or other body passages.

Although not illustrated in particular, in certain environments it may be desirable to provide a retaining structure at each longitudinal end of the stent to resist movement in the duct in which it is disposed.

While the invention has been described in connection with what is presently considered to be the most practical and preferred embodiment, it is to be understood that the invention is not to be limited to the disclosed embodiment, but on the contrary is intended to cover various modifications and equivalent arrangements included within the spirit and scope of the appended claims.

What is claimed is:

1. A method of providing for flow through a biological duct having a portion that is at least partially obstructed or constricted, comprising the steps of:

providing a structure comprising:
      an elongated main body member having first and second longitudinal ends and a longitudinal axis extending therebetween; and a plurality of wing elements projecting outwardly from said main body member, said wing elements being substantially uniformly distributed about an outer circumference of said main body member, each said wing element extending in a helical configuration along said main body member so as to have a length greater than the length of said main body member, each said wing member having first and second longitudinal side faces along which fluid flows due to the action of surface tension provided by such side faces; and inserting said structure into the biological duct so that it extends along at least a substantial portion of the constricted or partially obstructed portion thereof;

whereby biological fluid is enabled to flow along said side faces of said wing members and further whereby axial displacement of said structure within said duct is resisted.

2. A method as in claim 1, wherein said step of providing a structure comprises providing a structure having a plurality of non-perforated wing elements.

3. A method as in claim 1, wherein said step of providing a structure comprises providing a structure having a plurality of wing elements, at least one of which has a plurality of longitudinally extending grooves defined along at least a portion of a side face thereof.

4. A method as in claim 1, wherein said step of providing a structure comprises providing a structure having a plurality of radially extending wing elements.

5. A method as in claim 1, further comprising the step of coating said wing elements with a hydrophilic substance.

6. A method as in claim 1, further comprising the step of coating said wing elements with a therapeutic substance.

7. A stent comprising:

an elongated main body member having first and second longitudinal ends and a longitudinal axis extending therebetween;

a plurality of wing elements projecting outwardly from said main body member, said wing elements being substantially uniformly distributed about an outer circumference of said main body member, each said wing element extending in a helical configuration along said main body member so as to have a length greater than the length of said main body member, each said wing member having first and second longitudinal side faces along which fluid flows due to the action of surface tension provided by such side faces.

8. The stent of claim 7, wherein said longitudinal side faces are coated with a hydrophilic substance.

9. The stent of claim 7, wherein said longitudinal side faces are coated with a therapeutic substance.

10. The stent of claim 7, wherein said wing elements are non-perforated.

11. The stent of claim 7, wherein at least one of said wing elements has a plurality of longitudinally extending grooves defined along at least a portion of a side face thereof.

12. The stent of claim 7, wherein said wing elements extend radially outwardly.

* * * * *